US010092493B2

(12) United States Patent
Kim et al.

(10) Patent No.: US 10,092,493 B2
(45) Date of Patent: Oct. 9, 2018

(54) COMPOSITION OF SKIN EXTERNAL APPLICATION FOR ANTI-AGING

(71) Applicant: AMOREPACIFIC CORPORATION, Seoul (KR)

(72) Inventors: Jeong Ki Kim, Yongin-si (KR); Hyun Jung Shin, Anyang-si (KR); Su Nam Kim, Gangneung-si (KR); Byeong Gon Lee, Suwon-si (KR); Ih Seop Chang, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 0 days.

(21) Appl. No.: 15/058,681

(22) Filed: Mar. 2, 2016

(65) Prior Publication Data

US 2016/0175217 A1  Jun. 23, 2016

Related U.S. Application Data

(63) Continuation of application No. 12/064,887, filed as application No. PCT/KR2006/003571 on Sep. 8, 2006, now abandoned.

(30) Foreign Application Priority Data

Sep. 8, 2005  (KR) .......................... 10-2005-0083665
Sep. 8, 2005  (KR) .......................... 10-2005-0083667
Mar. 8, 2006  (KR) .......................... 10-2006-0021797

(51) Int. Cl.
A61K 8/49 (2006.01)
A61Q 19/08 (2006.01)
A61K 8/44 (2006.01)

(52) U.S. Cl.
CPC .............. A61K 8/498 (2013.01); A61K 8/442 (2013.01); A61Q 19/08 (2013.01); A61K 2800/592 (2013.01)

(58) Field of Classification Search
None
See application file for complete search history.

(56) References Cited

U.S. PATENT DOCUMENTS

| 5,589,505 A | 12/1996 | Yu et al. |
| 6,248,341 B1 | 6/2001 | Anderson et al. |
| 6,455,057 B1 | 9/2002 | Barrett et al. |
| 2003/0175234 A1 | 9/2003 | Hernandez et al. |
| 2003/0229030 A1 | 12/2003 | Theoharide |
| 2005/0031737 A1 | 2/2005 | Lines et al. |
| 2006/0134155 A1 | 6/2006 | Dryer et al. |

FOREIGN PATENT DOCUMENTS

| DE | 198 24 727 | 12/1999 |
| JP | 2002-516835 | 6/2002 |
| JP | 2002-265359 | 9/2002 |
| JP | 2003-252745 | 9/2003 |
| JP | 2004-67551 | 3/2004 |
| JP | 2004-284999 | 10/2004 |
| KR | 10-2002-0013978 | 2/2002 |
| KR | 10-0439627 | 7/2004 |
| KR | 10-2005-0000945 | 1/2005 |
| KR | 10-2005-0100472 | 10/2005 |
| WO | WO 01/49285 | 7/2001 |
| WO | WO 2004/014413 | 2/2004 |
| WO | WO 2004/093865 | 11/2004 |

OTHER PUBLICATIONS

International Search Report for PCT/KR2006/003571, dated Dec. 11, 2006.
Notice of Preliminary Rejection and English translation in KR 10-2006-0021797 dated Dec. 27, 2012.
Office Action and English translation in KR 10-2006-0021797 dated Aug. 30, 2013.
Official Action w/English translation in JP 2008-529922 dated Feb. 28, 2012.
Yoon et al., "Long-term Topical Oestrogen Treatment of Sun-exposed Facial Skin in Post-menopausal Women Does Not Improve Facial Wrinkles or Skin Elasticity, But Induces Matrix Metalloproteinase-1 Expression" *Acta Derm Venereol* 2014; 94: 4-8.

*Primary Examiner* — Bong-Sook Baek
(74) *Attorney, Agent, or Firm* — Nixon & Vanderhye P.C.

(57) ABSTRACT

The present invention relates to an anti-aging composition for external use on skin, and more particularly, to an anti-aging composition for external use on skin comprising at least one of catechins and flavonols as an active ingredient to inhibit decomposition and promote generation or protection at the dermis-epidermis junction.

5 Claims, 1 Drawing Sheet

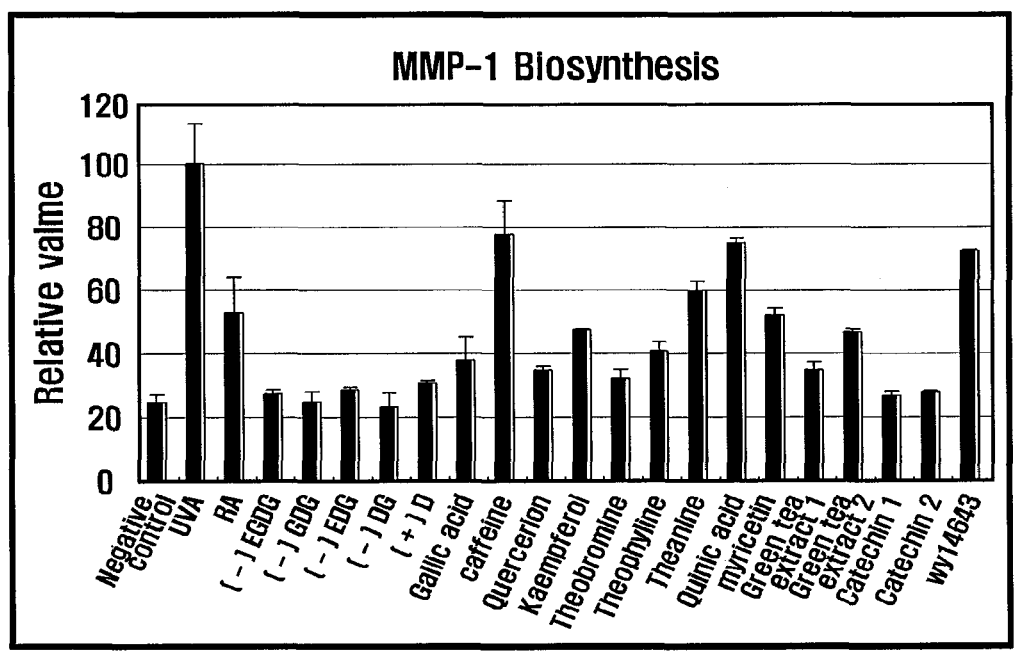

COMPOSITION OF SKIN EXTERNAL APPLICATION FOR ANTI-AGING

This application is a continuation of U.S. application Ser. No. 12/064,887, filed Aug. 11, 2008, which is a national phase of PCT/KR2006/003571, filed Sep. 8, 2006, which claims the benefit of Korean Patent Application Nos. 10-2006-0021797, filed Mar. 8, 2006, 10-2005-0083665, filed Sep. 8, 2005 and 10-2005-0083667 filed Sep. 8, 2005, the contents of each of which are incorporated herein by reference.

TECHNICAL FIELD

The present invention relates to an anti-aging composition for external use on skin, and more particularly, to an anti-aging composition for external use on skin comprising at least one of catechins and flavonols as an active ingredient to inhibit decomposition and promote generation or protection at the dermis-epidermis junction.

Also, it is possible to obtain synergy effect on anti-aging by using the green tea extract in combination with theanine.

BACKGROUND ART

The skin which is a primary barrier of the human body protects organs in the body from change of temperature and humidity and stimulation from the outer environment such as UV rays and pollutants and plays an important role for homeostasis such as regulation of body temperature. However, excessive physical and chemical stimulation from the outside, UV rays, stress and malnutrition may deteriorate normal functions of the skin and promote skin aging such as elasticity loss, keratinization and wrinkle formation. Particularly, the dermis-epidermis junction is severely damaged by UV irradiation.

As a result of the observation of change in the skin by aging, it has been found that the change in the structure of the dermis-epidermis junction such as multiplication and heat insulation already begins in the skin exposed to UV rays from late twenties. Therefore, it can be expected that generation of gelatinase (MMP-2, MMP-9) is induced at the epidermis of the human skin exposed to UV rays and associated with the damage of the dermis-epidermis junction. Further, in the research using mouse wrinkle model induced by UV-B irradiation for a long period of time, it has been found that gelatinase formed in the epidermis by UV-B irradiation may cause damage of the dermis-epidermis junction, damage of dermis and wrinkle formation. Meanwhile, the skin which has been seldom exposed to UV rays does not show such multiplication and heat insulation even at the advanced age.

Gelatinase (MMP-2, MMP-9) is an enzyme to decompose type IV collagen, type VII collagen and other extracellular matrix which are components of the dermis-epidermis junction. According to the analysis according to Gelatine zymography and Enzyme Linked Immunosorbent Assay (ELISA), MMP-2 and MMP-9 are detected in the UV-exposed epidermis. The activity of gelatinase in the skin is detected near epidermal stratum basalis and stratum spinosum in the chilled forehead skin. Moreover, gelatinase is detected in the epidermis of the UV-exposed skin such as the face. Therefore, it is believed that UV rays induce formation of gelatinase in the epidermal stratum basalis, a part of them participates in destruction of the dermis-epidermis junction and the rest stays in the epidermis and reaches the epidermis.

Upon examination of the wrinkle formation mechanism in the wrinkle model produced by irradiating UV rays to a mouse for a long period of time, gelatinase activity is detected throughout the epidermis in the skin exposed to UV-B for a long period of time. The damage of the dermis-epidermis junction is observed from the fifth week of UV-B irradiation and becomes severe upon the seventh and tenth week. Upon the tenth week, heat insulation is observed in the dermis barrier and multiplication is observed in a part. Upon examination of collagen fiber of the dermal mammillary portion, reduction of fiber density is observed by UV-B irradiation for a long period of time. Therefore, it has been provided that the induced gelatinase is involved in damage of the dermis-epidermis junction and collagen decomposition of the mammillary dermis.

When the dermis-epidermis junction is damaged, wrinkle is formed by flattering of the junction, multiplication and heat insulation, and the skin is sagged and is apt to be damaged. Also, by the loss of the characteristic barrier function, the dermis-epidermis junction fails to filter pollutants from the outer environment, whereby noxious materials can readily infiltrate to the dermis and the skin can be damaged. In order to recover the damaged dermis-epidermis junction or maintain it at the healthy state, its components should be maintained as they are. The components which is known that whose biosynthesis is decreased, as the age increases, are type IV collagen, type VII collagen and laminin 10/11. Laminin 5 does not shown change while the components whose biosynthesis is increased are gelatinase (MMP-2 and MMP-9) which is known to be associated with decomposition (Lavker et. Al. J. Invest. Derm. 1979, 73:59-65, Pouliot et. Al. Exp. Dermatol. 2002, 11:387-397).

In order to prevent the skin aging by UV irradiation and outer stress and maintain healthy and elastic skin, there have been efforts to maintain peculiar function of the skin and activate skin cells to effectively inhibit the skin aging by using cosmetic composition supplemented with physiological activating materials obtained from animals, plants and microorganisms.

DISCLOSURE

Technical Problem

Accordingly, the present inventors have searched a method for effectively controlling various factors affecting skin aging and found that various change of the junction between the dermis and epidermis caused by natural aging and photo-aging, including degeneration, heat insulation and multiplication, can be prevented or recovered by using a composition for external use on skin comprising at least one of catechins and flavonols which are extracted from green tea. Thus, it has been confirmed that catechins or flavonols from the green tea extract can inhibit the decomposition and promote the generation at the dermis-epidermis junction, thereby strengthening the bonding between the dermis and the epidermis, whereby they can be used in cosmetic preparations and pharmaceutical compositions for anti-aging.

Also, it has been found that if theanine is combined into the components from the green tea extract, even when the green tea extract is mixed with theanine at a low concentration, the combination can show high anti-aging effect without side effects on the skin. On the basis of the above findings, the present invention has been completed.

Therefore, it is an object of the present invention to provide a composition for external use on skin with excellent anti-aging effect.

Technical Solution

To accomplish the above objects of the present invention, according to the present invention, there is provided a composition for external use on skin with excellent anti-aging effect comprising at least one of catechins and flavonols as an active ingredient.

Also, in another embodiment of the present invention, there is provided a composition for external use on skin with excellent anti-aging effect comprising theanine in addition to the above-described components from the green tea extract as an active ingredient.

Advantageous Effects

The composition for external use on skin according to the present invention comprising at least one of catechins and flavonols of the green tea extract as an active ingredient can reduce biosynthesis of gelatinase (MMP-2, MMP-9) and increase biosynthesis of type IV collagen, type VII collagen and laminin 10/11 to inhibit the decomposition and promote the generation at the dermis-epidermis junction, thereby protect the dermis-epidermis junction.

DESCRIPTION OF DRAWINGS

Further objects and advantages of the invention can be more fully understood from the following detailed description taken in conjunction with the accompanying drawing, in which:

FIG. 1 is a graph showing the result of the measurement of MMP-1 biosynthesis by various test samples.

BEST MODE

The composition for external use on skin according to the present invention comprises at least one of catechins and flavonols from the green tea extract as an active ingredient.

The catechins used according to the present invention is extracted from green tea and includes epigallocatechin gallate (EGCG), gallocatechin gallate (GCG), epicatechin gallate (ECG), catechin gallate (CG), epigallocatechin (EGC), gallocatechin (GC), (−)epicatechin (EC), (+)epicatechin (EC), (−)catechin (CA) and (+)catechin (CA), with preference being epigallocatechin gallate (EGCG), gallocatechin gallate (GCG), epicatechin gallate (ECG) and catechin gallate (CG) expressed by the following formulae 1 to 4.

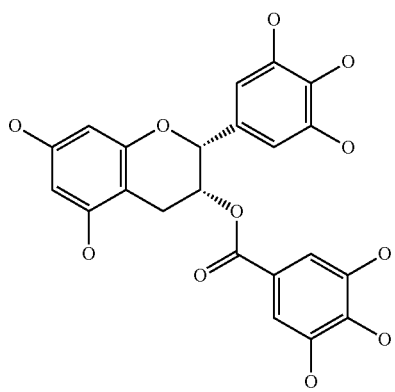

[Formula 1]

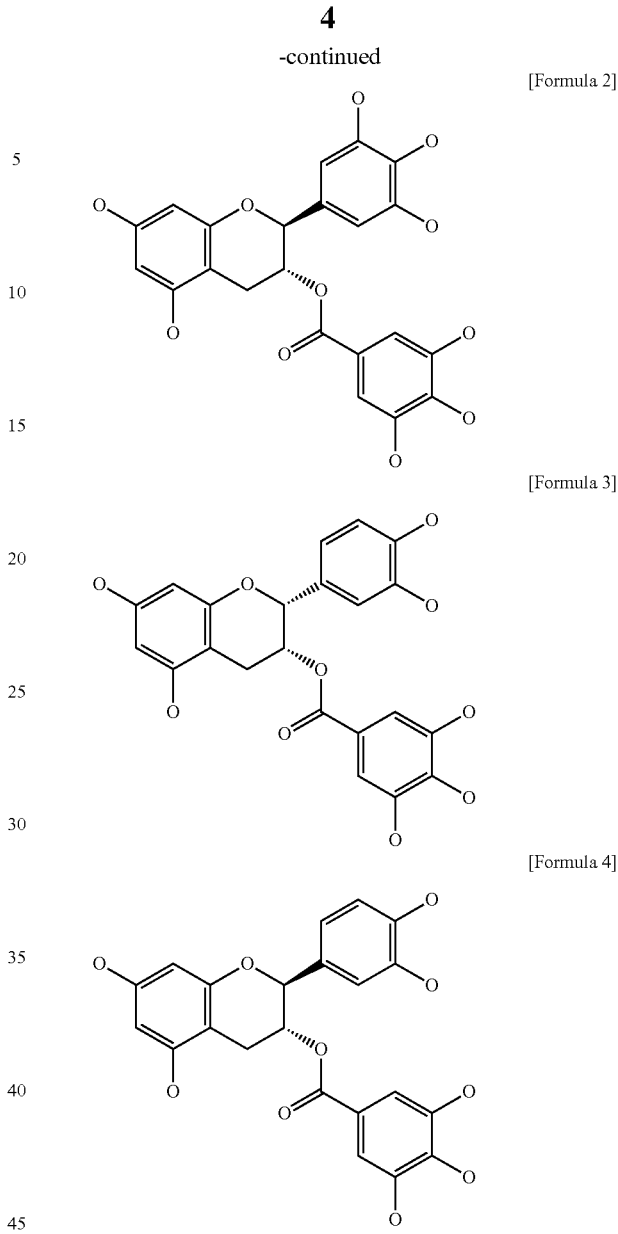

[Formula 2]

[Formula 3]

[Formula 4]

Also, the flavonols used according to the present invention is extracted from green tea and includes quercetin, kaempferol and myricetin, with preference being kaempferol and myricetin, more preference being myricetin.

The composition for external use according to the present invention comprises 0.001 to 10 wt %, preferably 0.01 to 5 wt % of the active ingredient, based on the total weight of the composition. If the content is less than 0.001 wt %, it is difficult to expect significant effects, while if the content excesses 10 wt %, it is impossible to formulate the composition.

According to another aspect, there is provided a composition for external use on skin further comprising theanine as an active ingredient, in addition to the component from the green tea extract.

Theanine is one of amino acids giving savory taste of green tea and has effect of inhibiting excitation caused by caffeine. In fact, it has been observed that human bodies intaking theanine shows increase in a wave appearance showing stabilized and tranquil state of mind (Nippon Nogeikagaku Kaishi, 1998, 72 (2): 153-157). The theanine used according to the present invention may be one selected from L-form which is extracted from green tea, and L-theanine, D-theanine and DL-theanine which are chemically synthesized, or may be prepared other methods.

When the composition for external use on skin according to the present invention comprises theanine in combination with at least one of catechins and flavonols from the green tea extract, it is possible to effectively and generally improve several symptoms such as wrinkle and sagging. Particularly, the content of at least one of catechins and flavonols from the green tea extract in the composition is determined from the result of in vitro experiments and in vivo experiments and is preferably 0.0004 to 0.025 wt %, based on the total weight of the composition. Here, if the content is less than 0.0004 wt % the component cannot act as an effective ingredient, while if the content excesses 0.025 wt % the improvement of the symptoms is rather deteriorated.

Also, the content of theanine is determined from the result of in vitro experiments and in vivo experiments and is preferably 0.008 to 2.5 wt %, based on the total weight of the composition. Here, if the content is less than 0.008 wt %, the component cannot act as an effective ingredient, while if the content excesses 2.5 wt % the improvement of the symptoms is rather deteriorated.

Further, the composition for external use on skin according to the present invention comprises the green tea extract and theanine in a predetermined mixing ratio. Thus, when the composition contains 0.0004 to 0.025 wt % of the green tea extract, catechin to theanine is 1:20 to 1:100 for optimal anti-aging effect of skin.

The composition for external use on skin according to the present invention prevent and improve skin aging through promotion of collagen synthesis, improvement skin elasticity and improvement of skin wrinkles.

Also, the composition for external use on skin according to the present invention activates peroxisome proliferator-activated receptor-alpha (PPAR-α) to inhibit tumor necrosis factor α (TNF-α) and biosynthesis of MMP-1, thereby inhibiting skin aging.

Peroxisome is one of organelles providing causes of abnormal metabolic functions leading hyperlipidemia, diabetes and obesity. For a long time, this organelle has been considered to play a tiny role in the cell. However, according to many recent studies, it has been reported that it plays very important role in control of cell multiplication/differentiation, control of inflammatory mediators and the like and widely affects metabolism of oxygen, glucose, lipid and hormones. It has been found that peroxisome affects the formation of the cell membrane and adipocyte as well as insulin sensitivity, through lipid metabolism and glucose metabolism and plays an important role in aging and tumorigenesis through action on oxidative stress (J Cutan Med Sirg 5 (3):231-43, 2001, J Cutan Med Sirg 5 (4):315-22, 2001).

The intensive research on the above-described part for the last 10 years has presented several evidences that peroxisome proliferator-activated receptos (PPARs), hereinafter referred to as 'PPAR'), a nuclear hormone receptor would be a good target for pharmacological approach for above-described diseases. According to the resent studies, PPARs, particularly PPAR-α, a one of subtypes, play critical roles in promotion of differentiation/inhibition of multiplication of keratinocyte, promotion of dermal barriers through lipid metabolism and inhibition of inflammation at epidermis of skin and inhibit inflammatory mediators formation of PPAR-α and erythema formation by UV irradiation (JID 117 (6):1430-6, 2001).

The present inventors have exams general information on biology of these PPARs and effects and working mechanism of PPAR-α on skin, particularly relation with skin aging to find a ligand capable of inducing activation. As a result, it has been found that by using the composition for external use on skin according to the present invention, it is possible to inhibit inflammation induced by natural aging and photo-aging, thereby preventing or recovering skin aging. Thus, it has been proved that the composition for external use according to the present invention can inhibit expression of matrix metalloproteinase-1, an enzyme to decompose the dermis by inflammation inhibiting mechanism through activation of PPAR-α.

The composition for external use according to the present invention is not particularly limited in its formulation but may be cosmetic compositions including, for example, skin softener, skin lotion, massage cream, nourishing cream, pack, gel or skin adhesive type cosmetic formulations, or transdermal formulations such as lotion, ointment, gel, cream, patch or spray.

Also, the composition for external use in various formulation types may comprise the above-described essential components in combination with other components which may be selected by the workers in the art without any difficulty according to the formulation type or the purpose of use.

Mode for Invention

Now, the construction and effect of the present invention will be explained in detail by Examples and Experimental examples. However, it should be understood that these examples are only for explanation and the present invention is not limited thereto.

[Reference Example 1] Preparation of Green Tea Extract 1

100 g of dried green tea leaves was taken into 10 times ethanol for 12 to 15 hours at ambient temperature for extraction, followed by filtration through filter paper. The filtrate was concentrated at 50□ at reduced pressure.

[Reference Example 2] Preparation of Green Tea Extract 2

100 g of dried green tea leaves was taken into 10 times ethanol for 12 to 15 hours at ambient temperature for extraction, followed by filtration through filter paper. The filtrate was concentrated at 50□ at reduced pressure.

[Experimental Example 1] Measurement of Inhibiting Effect on Biosynthesis of Gelatinase A (MMP-9) and Gelatinase B (MMP-2) by UV Irradiation Human keratinocytes were cultured in a 24-well plate type incubator at a concentration of $10^4$. After 24 hours, the plate was irradiated by UV-B at 30 mJ/cm$^2$. The media were exchanged with new medium containing 10 ppm of each test substance. After 2 days of cultivation, each supernatant was harvested and subjected to the zymography using gelatine gel to obtain produced MMP-2 and MMP-9, quantities of which were then measured by a densitometer. The data were calculated as comparative values, referred to 100 of UV control and the result is shown in Table 1.

TABLE 1

| Ingredients | MMP-2 (%) | MMP-9 (%) |
|---|---|---|
| Myricetin | 51 | 55 |
| EGCG | 52 | 56 |
| GCG | 53 | 56 |
| CG | 53 | 55 |
| Green tea extract 1 | 48 | 49 |
| Green tea extract 2 | 61 | 62 |
| Green tea catechin extract 1 | 55 | 59 |
| Green tea catechin extract 2 | 62 | 60 |
| Control | 100 | 100 |

From the result of Table 1, it was confirmed that the active ingredient used as an active ingredient in the present invention, myricetin, epigallocatechin gallate (EGCG), gallocatechin gallate (GCG), epicatechin gallate (ECG), catechin gallate (CG), green tea catechin extract and green tea extract reduced biosynthesis of MMP-2 and MMP-9, enzymes to decompose type IV collagen and type VII collagen of dermal matrix, thereby preventing decomposition of the dermis-epidermis junction.

[Experimental Example 2] Measurement of Effect on Biosynthesis of Type IV Collagen in Dermal Cell Human keratinocytes were cultured in a 24-well plate type incubator at a concentration of $5 \times 10^4$. The media were exchanged with new medium containing 10 ppm of each test substance. After 24 hours of cultivation, each supernatant was harvested and subjected to the Dot Blot method to measure the amount of produced type IV collagen. The data were calculated as comparative values, referred to 100 of UV control and the result is shown in Table 2.

TABLE 2

| Ingredients | Type IV collagen biosynthesis (%) |
|---|---|
| Myricetin | 139 |
| EGCG | 138 |
| GCG | 135 |
| CG | 134 |
| Green tea extract 1 | 140 |
| Green tea extract 2 | 139 |
| Green tea catechin extract 1 | 145 |
| Green tea catechin extract 2 | 143 |
| Control | 100 |

From the result of Table 2, it was confirmed that the active ingredient used as an active ingredient in the present invention, myricetin, epigallocatechin gallate (EGCG), gallocatechin gallate (GCG), epicatechin gallate (ECG), catechin gallate (CG), green tea catechin extract and green tea extract increased biosynthesis of type IV collagen.

[Experimental Example 3] Measurement of Effect on Biosynthesis of Type VII Collagen in Dermal Cell Human fibroblasts were cultured in a 24-well plate type incubator at a concentration of $10^4$. The media were exchanged with new medium containing 10 ppm of each test substance. After 24 hours of cultivation, each supernatant was harvested and subjected to the Dot Blot method to measure the amount of produced type VII collagen. The data were calculated as comparative values, referred to 100 of UV control and the result is shown in Table 3.

TABLE 3

| Ingredients | type VII collagen biosynthesis (%) |
|---|---|
| Myricetin | 125 |
| EGCG | 127 |
| GCG | 121 |
| CG | 124 |
| Green tea extract 1 | 132 |
| Green tea extract 2 | 128 |
| Green tea catechin extract 1 | 131 |
| Green tea catechin extract 2 | 127 |
| Control | 100 |

From the result of Table 3, it was confirmed that the active ingredient used as an active ingredient in the present invention, myricetin, epigallocatechin gallate (EGCG), gallocatechin gallate (GCG), epicatechin gallate (ECG), catechin gallate (CG), green tea catechin extract and green tea extract increased biosynthesis of type VII collagen.

[Experimental Example 4] Measurement of Effect on Biosynthesis of Laminin 10/11 in Dermal Cell Human keratinocytes were cultured in a 24-well plate type incubator at a concentration of $5 \times 10^4$. The media were exchanged with new medium containing 10 ppm of each test substance. After 24 hours of cultivation, each supernatant was harvested and subjected to the Western Blot method to measure the amount of produced laminin 10/11. The data were calculated as comparative values, referred to 100 of UV control and the result is shown in Table 4.

TABLE 4

| Ingredients | laminin 10/11 biosynthesis (%) |
|---|---|
| Myricetin | 132 |
| EGCG | 137 |
| GCG | 131 |
| CG | 129 |
| Green tea extract 1 | 137 |
| Green tea extract 2 | 133 |
| Green tea catechin extract 1 | 139 |
| Green tea catechin extract 2 | 142 |
| Control | 100 |

From the result of Table 4, it was confirmed that the active ingredient used as an active ingredient in the present invention, myricetin, epigallocatechin gallate (EGCG), gallocatechin gallate (GCG), epicatechin gallate (ECG), catechin gallate (CG), green tea catechin extract and green tea extract increased biosynthesis of laminin 10/11.

[Experimental Example 5] Measurement of Change at Dermis-Epidermis Junction in Nude Mouse In order to confirm the change at the dermis-epidermis junction by UV irradiation after use of the composition according to the present invention, Examples 1 to 9 and Comparative example 1 were prepared in a nourishing cream formulation as shown in Table 5 and applied on the back of a nude mouse 5 times per week for 2 weeks. Then, the formulations were applied 5 times on the back while the back was irradiated with UV 3 times per week for 12 weeks. Through biopsy, the change at the dermis-epidermis junction was examined using an electron microscope.

TABLE 5

| Ingredients (wt %) | Example 1 | 1-1 | 1-2 | 2 | 3 | 4 | 5 | 6 | 7 | 8 | 9 | Com. Ex. 1 |
|---|---|---|---|---|---|---|---|---|---|---|---|---|
| Purified water | Bal. | Bal. | Bal. | Bal. | Bal. | Bal. | Bal. | Bal. | Bal. | Bal. | Bal. | Bal. |
| Myricetin | 0.1 | 0.2 | 0.5 | 0.1 | 0.1 | 0.1 | 0.1 | 0.1 | 0.1 | 0.1 | 0.1 | — |
| EGCG | — | — | — | 0.1 | — | — | — | — | — | — | 0.1 | — |
| GCG | — | — | — | — | 0.1 | — | — | — | — | — | 0.1 | — |
| CG | — | — | — | — | — | 0.1 | — | — | — | — | — | — |
| Green tea extract 1 | — | — | — | — | — | — | 0.1 | — | — | — | — | — |
| Green tea extract 2 | — | — | — | — | — | — | — | 0.1 | — | — | — | — |
| Green tea catechin extract 1 | — | — | — | — | — | — | — | — | 0.1 | — | — | — |
| Green tea catechin extract 2 | — | — | — | — | — | — | — | — | — | 0.1 | — | — |
| Hydrogenated vegetable oil | 1.50 | 1.50 | 1.50 | 1.50 | 1.50 | 1.50 | 1.50 | 1.50 | 1.50 | 1.50 | 1.50 | 1.50 |
| Stearic acid | 0.60 | 0.60 | 0.60 | 0.60 | 0.60 | 0.60 | 0.60 | 0.60 | 0.60 | 0.60 | 0.60 | 0.60 |
| Glycerol stearate | 1.00 | 1.00 | 1.00 | 1.00 | 1.00 | 1.00 | 1.00 | 1.00 | 1.00 | 1.00 | 1.00 | 1.00 |
| Stearyl alcohol | 2.00 | 2.00 | 2.00 | 2.00 | 2.00 | 2.00 | 2.00 | 2.00 | 2.00 | 2.00 | 2.00 | 2.00 |
| Polyglyceril-10/penta stearate/behenyl alcohol/sodium stearoyl lactylate | 1.00 | 1.00 | 1.00 | 1.00 | 1.00 | 1.00 | 1.00 | 1.00 | 1.00 | 1.00 | 1.00 | 1.00 |
| Arakidyl behenyl alcohol/arakidyl glucoside | 1.00 | 1.00 | 1.00 | 1.00 | 1.00 | 1.00 | 1.00 | 1.00 | 1.00 | 1.00 | 1.00 | 1.00 |
| Cetylaryl alcohol/cetelaryl glucoside | 2.00 | 2.00 | 2.00 | 2.00 | 2.00 | 2.00 | 2.00 | 2.00 | 2.00 | 2.00 | 2.00 | 2.00 |
| PEG-100 stearate/glycerololate/propylene glycol | 1.50 | 1.50 | 1.50 | 1.50 | 1.50 | 1.50 | 1.50 | 1.50 | 1.50 | 1.50 | 1.50 | 1.50 |
| Caprylic and capric triglyceride | 11.00 | 11.00 | 11.00 | 11.00 | 11.00 | 11.00 | 11.00 | 11.00 | 11.00 | 11.00 | 11.00 | 11.00 |
| Cyclomedicone | 6.00 | 6.00 | 6.00 | 6.00 | 6.00 | 6.00 | 6.00 | 6.00 | 6.00 | 6.00 | 6.00 | 6.00 |
| Preservative, flavor | * | * | * | * | * | * | * | * | * | * | * | * |
| Triethanol amine | 0.1 | 0.1 | 0.1 | 0.1 | 0.1 | 0.1 | 0.1 | 0.1 | 0.1 | 0.1 | 0.1 | 0.1 |

Bal.: balance,
*: suitable amount

As a result, when the cosmetic formulations of Examples 1-9 were applied along with UV irradiation, there was hardly observed deformation, separation, isolation and multiplication at the dermis-epidermis junction, as compared to Comparative example. From the result, it was confirmed that the active ingredient used as an active ingredient in the present invention, myricetin, epigallocatechin gallate (EGCG), gallocatechin gallate (GCG), epicatechin gallate (ECG), catechin gallate (CG), green tea catechin extract and green tea extract reduce wrinkles on skin and strengthen elasticity and the result is shown in Table 6.

Particularly, when myricetin is used in combination with epigallocatechin gallate (EGCG), gallocatechin gallate (GCG), epicatechin gallate (ECG), catechin gallate (CG), green tea catechin extract and green tea extract, the effect was better, as compared to the case when myricetin is used alone. Also, it was more preferable to use myricetin at a low concentration in combination with catechin, as compared to the case when it is used alone at a high concentration.

TABLE 6

Change at the dermis-epidermis junction

| | Example | | | | | | | | | | | Com. Ex. |
|---|---|---|---|---|---|---|---|---|---|---|---|---|
| | 1 | 1-1 | 1-2 | 2 | 3 | 4 | 5 | 6 | 7 | 8 | 9 | 1 |
| Multiplication | + | + | + | + | +/− | +/− | +/− | +/− | +/− | +/− | +/− | ++++ |
| Heat insulation | + | + | + | + | +/− | +/− | +/− | +/− | +/− | +/− | +/− | ++++ |

+/−: no change,
+: little,
++: mild,
+++: significant,
++++: very significant

[Experimental Example 6] Measurement of Effect on Biosynthesis of Collagen in Dermal Cell Human fibroblasts were cultured in a 48-well plate type incubator at a concentration of $10^4$. The media were exchanged with new medium (theanine: 1, 10, 100 um) containing each test substance of Table 7 at a concentration of 0.001 μM, 0.01 μM, 0.1 μM, 0.5 μM and 2 μM. After 48 hours of cultivation, each supernatant was harvested and subjected to ELISA (Takara MK101) to measure the amount of produced pro-collagen. The data were calculated as comparative values, referred to 100 of un-treated control and the result is shown in Table 7.

TABLE 7

| | Concentration | Collagen biosynthesis |
|---|---|---|
| (−) EGCG | 0.001 μM | 101.4 |
| | 0.01 μM | 154.6 |
| | 0.1 μM | 133.8 |
| | 0.5 μM | 155.8 |
| | 2 μM | 78.4 |
| (−) GCG | 0.001 μM | 98.9 |
| | 0.01 μM | 138.3 |
| | 0.1 μM | 147.0 |
| | 0.5 μM | 157.1 |
| | 2 μM | 75.2 |
| (−) ECG | 0.001 μM | 100.5 |
| | 0.01 μM | 181.7 |
| | 0.1 μM | 165.3 |
| | 0.5 μM | 124.5 |
| | 2 μM | 77.8 |
| (−) CG | 0.001 μM | 104.3 |
| | 0.01 μM | 118.5 |
| | 0.1 μM | 124.9 |

TABLE 7-continued

|  | Concentration | Collagen biosynthesis |
|---|---|---|
| Theanine | 0.5 µM | 118.9 |
|  | 2 µM | 80.3 |
|  | 1 µM | 13.5 |
|  | 10 µM | 132.1 |
|  | 100 µM | 167.5 |

From the result of Table 7, it was confirmed that catechin or theanine increased biosynthesis of collagen even at a low concentration.

Also, in order to examine the synergic effect of theanine on collagen biosynthesis, theanine 10 µM was added to catechin at different 4 concentrations and the result is shown in Table 8.

TABLE 8

|  | Catechin concentration | Collagen biosynthesis |
|---|---|---|
| (−)EGCG + theanine 10 µM | 0.01 µM | 157.1 |
|  | 0.1 µM | 164.6 |
|  | 0.5 µM | 168.1 |
|  | 1 µM | 132.4 |
| (−)GCG + theanine 10 µM | 0.01 µM | 158.0 |
|  | 0.1 µM | 167.5 |
|  | 0.5 µM | 165.8 |
|  | 1 µM | 142.3 |
| (−)ECG + theanine 10 µM | 0.01 µM | 166.3 |
|  | 0.1 µM | 180.4 |
|  | 0.5 µM | 178.2 |
|  | 1 µM | 122.4 |
| (−)CG + theanine 10 µM | 0.01 µM | 120.7 |
|  | 0.1 µM | 144.7 |
|  | 0.5 µM | 148.0 |
|  | 1 µM | 113.2 |

From the result of Table 8, it was confirmed that the optimal concentration of catechin to theanine 10 µM was 0.1 to 0.5 µM and thus, the optimal content ratio of catechin to theanine was 1:20 to 1:100.

[Experimental Example 7] Improvement of Wrinkles in Human

In order to confirm the improvement effect of nourishing cream prepared according to the compositions of Comparative examples 2 to 7 and Examples 10 to 13 in Table 9, the following procedures were performed. 100 women in thirties were classified into 10 groups of 10 members and each was treated with the formulations of Comparative examples 2 to 7 and Examples 10 to 13. Replicas were taken using silicone and the wrinkle state was assayed on a visiometer (SV600, Courage+Khazaka electronic GmbH, Germany). The result is shown in Table 10. The values of Table 10 are averages of the difference between parameters of after application for 8 weeks and before application.

TABLE 9

| Ingredients (content; wt %) | Ex. 10 | Ex. 11 | Ex. 12 | Ex. 13 | Com. Ex.2 | Com. Ex.3 | Com. Ex.4 | Com. Ex.5 | Com. Ex.6 | Com. Ex.7 |
|---|---|---|---|---|---|---|---|---|---|---|
| Purified water | Bal. | Bal. | Bal. | Bal. | Bal. | Bal. | Bal. | Bal. | Bal. | Bal. |
| (−)EGCG | 0.0025 | — | — | — | 0.1 | — | — | — | 0.5 | — |
| (−)GCG | — | 0.0004 | — | — | — | 0.5 | — | — | — | 1 |
| (−)ECG | — | — | 0.002 | — | — | — | 0.1 | — | — | — |
| (−)CG | — | — | — | 0.025 | — | — | — | 0.1 | — | — |
| theanine | 0.01 | 0.01 | 0.1 | 2.5 | 0.01 | 0.01 | 0.1 | 5.0 | 5.0 | 5.0 |
| Hydrogenated vegetable oil | 1.50 | 1.50 | 1.50 | 1.50 | 1.50 | 1.50 | 1.50 | 1.50 | 1.50 | 1.50 |
| Stearic acid | 0.60 | 0.60 | 0.60 | 0.60 | 0.60 | 0.60 | 0.60 | 0.60 | 0.60 | 0.60 |
| Glycerol stearate | 1.00 | 1.00 | 1.00 | 1.00 | 1.00 | 1.00 | 1.00 | 1.00 | 1.00 | 1.00 |
| Stearyl alcohol | 2.00 | 2.00 | 2.00 | 2.00 | 2.00 | 2.00 | 2.00 | 2.00 | 2.00 | 2.00 |
| Polyglyceril-10/penta stearate/ behenyl alcohol/ sodium stearoyl lactylate | 1.00 | 1.00 | 1.00 | 1.00 | 1.00 | 1.00 | 1.00 | 1.00 | 1.00 | 1.00 |
| Arakidyl behenyl alcohol/ arakidyl glucoside | 1.00 | 1.00 | 1.00 | 1.00 | 1.00 | 1.00 | 1.00 | 1.00 | 1.00 | 1.00 |
| Cetylaryl alcohol/cetelaryl glucoside | 2.00 | 2.00 | 2.00 | 2.00 | 2.00 | 2.00 | 2.00 | 2.00 | 2.00 | 2.00 |
| PEG-100 stearate/ glycerololate/ propylene glycol | 1.50 | 1.50 | 1.50 | 1.50 | 1.50 | 1.50 | 1.50 | 1.50 | 1.50 | 1.50 |
| Caprylic and capric triglyceride | 11.00 | 11.00 | 11.00 | 11.00 | 11.00 | 11.00 | 11.00 | 11.00 | 11.00 | 11.00 |
| Cyclomedicone | 6.00 | 6.00 | 6.00 | 6.00 | 6.00 | 6.00 | 6.00 | 6.00 | 6.00 | 6.00 |
| Preservative, flavor | * | * | * | * | * | * | * | * | * | * |
| Triethanol amine | 0.1 | 0.1 | 0.1 | 0.1 | 0.1 | 0.1 | 0.1 | 0.1 | 0.1 | 0.1 |

Bal.: balance,
*: suitable amount

TABLE 10

| Result after application for 8 weeks | R1 | R2 | R3 | R4 | R5 |
|---|---|---|---|---|---|
| Ex. 10 | −0.23 | −0.24 | −0.16 | −0.06 | −0.04 |
| Ex. 11 | −0.22 | −0.23 | −0.15 | −0.04 | −0.05 |
| Ex. 12 | −0.24 | −0.25 | −0.18 | −0.06 | −0.04 |
| Ex. 13 | −0.25 | −0.24 | −0.18 | −0.05 | −0.03 |
| Com. Ex. 2 | −0.16 | −0.18 | −0.13 | −0.04 | −0.03 |
| Com. Ex. 3 | −0.16 | −0.17 | −0.12 | −0.06 | −0.03 |
| Com. Ex. 4 | −0.15 | −0.15 | −0.13 | −0.02 | −0.04 |
| Com. Ex. 5 | −0.16 | −0.16 | −0.12 | −0.04 | −0.03 |
| Com. Ex. 6 | −0.05 | −0.08 | −0.12 | −0.06 | −0.04 |
| Com. Ex. 7 | −0.08 | −0.10 | −0.11 | −0.05 | −0.03 |

* R1: difference between the highest value and the lowest value of the wrinkle contour line,
R2: average of 5 R1 values of the wrinkle contour line randomly divided into 5 portions,
R3: the highest value of the 5 R1 values,
R4: average of the difference between the peak and the valley on the baseline of the wrinkle contour line,
R5: difference between the baseline of the wrinkle contour line and the wrinkle contour As shown in Table 10, it was confirmed that the compositions for external use comprising catechin and theanine in a predetermined mixing ratio according to Examples 10 to 13 showed excellent effect of improving skin wrinkle.

[Experimental Example 8] Improvement of Skin Elasticity in the Human Body

Nourishing creams prepared according to the compositions of Table 9 were examined for their effect to improve skin elastic. 100 healthy women over 30 years old were divided into 10 groups. Each group applied one of the nourishing cream of Comparative examples 2 to 7 and Examples 10 to 13 on the face twice per day at a temperature of 24-26□ and a humidity of 75% for cream for 12 weeks and was examined for skin elasticity using Cutometer SEM 575, (C+K Electronic Co., Germany). The result is shown in Table 11. The data of Table 11 are described as R8 (R8 (left)-R8 (right)) of the Cutometer SEM 575, in which R8 means skin viscoelasticity.

Separately, the members of the groups were asked to answer a questionnaire for subjective estimation in addition to the mechanical evaluation. The result is shown in Table 12.

TABLE 11

| Tested composition | Skin elasticity |
|---|---|
| Example 10 | 0.38 |
| Example 11 | 0.44 |
| Example 12 | 0.42 |
| Example 13 | 0.44 |
| Com. Ex. 2 | 0.35 |
| Com. Ex. 3 | 0.33 |
| Com. Ex. 4 | 0.32 |
| Com. Ex. 5 | 0.36 |
| Com. Ex. 6 | 0.29 |
| Com. Ex. 7 | 0.30 |

TABLE 12

| Test group | Number of respondents | | | |
|---|---|---|---|---|
| | Very good | Good | Fair | Poor |
| Example 10 | 4 | 3 | 2 | 1 |
| Example 11 | 4 | 4 | 1 | 1 |
| Example 12 | 4 | 3 | 3 | 0 |
| Example 13 | 3 | 5 | 1 | 1 |
| Com. Ex. 2 | 1 | 1 | 6 | 2 |
| Com. Ex. 3 | 1 | 2 | 4 | 3 |
| Com. Ex. 4 | 0 | 3 | 4 | 3 |
| Com. Ex. 5 | 1 | 2 | 5 | 2 |
| Com. Ex. 6 | 1 | 1 | 4 | 3 |
| Com. Ex. 7 | 1 | 1 | 5 | 3 |

As shown in Table 11, the groups treated with the compositions of Examples 10 to 13 comprising catechin and theanine at a low concentration showed more increase in the skin elasticity, as compared to the group treated with the composition of Comparative example.

Meanwhile, it was confirmed through the questionnaire that the skin elasticity was improved by application of the compositions of Examples 10 to 13 according to the present invention.

[Experimental Example 9 Test of Activation of PPAR-α (Peroxisome Proliferator Activated Receptor-alpha) Playing a Role in Promotion of Differentiation/Inhibition of Multiplication of Dermal Cells and Promotion of Lipid Biosynthesis and Prevention of Inflammation Monkey kidney epithelial cell line CV-1 (ATCC CCL 70) was subcultured in a DMEM medium containing 10% fetal bovine serum treated with charcol/dextran, which was a phenol red-free medium to remove the effect by estrogen of phenol red. Three different plasmids, each comprising a universal promoter capable of being expressed in a general culturing conditions and having PPAR-α gene in the down stream, a universal promoter having PPRE (PPARs Response Element), which is activated by bonding to PPAR-α of ligand bonding type, and firefly luciferase gene, which functions as a reporter and a universal promoter with Renilla luciferase gene attached as a reference were used.

CV-1 cells were distributed in a 24-well plate type incubator at a concentration of $5 \times 10^4$. After 24 hours cultivation, the 3 different plasmids were transient transfected. After 24 hours cultivation, the plate was washed with 1×PBS (Phosphate Buffered Saline) and treated with ligand candidates at various concentrations. After 24 hours cultivation, the plate was washed with 1×PBS and the cells were lyzed with 1×PLB (Passive Lysis Buffer) and measured for luciferase activity using Dual-Luciferase® Reporter Assay System kit.

In this experiment, the positive control was Wy-14,643 which was known to be most powerful PPAR-α ligand and the negative control was ethanol which was used to dissolve the samples and non-treated group. The result is shown in Table 13, with the data as comparative values referred to as 1.0 of the negative control and the non-treated group.

TABLE 13

| | Activity of PPAR-α | |
|---|---|---|
| | PPAR-α activity | |
| Test substances | 10 μM | 100 μM |
| (−) EGCG | 1.0 | 1.5 |
| (−) GCG | 1.1 | 2.3 |
| (−) ECG | 1.1 | 1.6 |

TABLE 13-continued

Activity of PPAR-α

| Test substances | PPAR-α activity | |
|---|---|---|
| | 10 μM | 100 μM |
| (−) CG | 1.2 | 1.6 |
| (−) EGC | 1.3 | 1.0 |
| (−) GC | 1.1 | 1.0 |
| (−) EC | 1.2 | 1.2 |
| (+) EC | 1.3 | 1.2 |
| (−) C | 1.4 | 1.2 |
| (+) C | 1.5 | 1.4 |
| Gallic acid | 1.3 | 1.7 |
| Caffeine | 1.3 | 1.6 |
| Quercetin | 1.7 | 2.3 |
| Kaempferol | 1.7 | 1.4 |
| Theobromine | 2.2 | 4.5 |
| Theophylline | 1.4 | 1.7 |
| Theanine | 1.8 | 1.9 |
| Rutin hydrate | 1.6 | 1.3 |
| Quinic acid | 1.3 | 1.7 |
| Myricetin | 1.7 | 1.6 |
| Green tea extract 1 | 1.7 | 3.2 |
| Green tea extract 2 | 1.7 | 2.3 |
| Catechin extract 1 | 1.7 | 4.6 |
| Catechin extract 2 | 1.9 | 4.8 |
| Positive control | 0.1 μM / 1.5 | 1 μM / 2.6 ... 10 μM / 3.8 |

From the above result, among the various components of green tea, green tea extract 1, green tea extract 2, catechin extract 1, catechin extract 2, gallocatechin gallate ((−)GCG), theobromine and quercetin showed significant activation of PPAR-α. (−)EGCG, (−)ECG, (−)CG, (+)C, gallic acid, caffeine, kaempferol, theophylline, theanine, quinic acid and myricetin were followed.

[Experimental Example 10] Measurement of Inhibition Effect on Biosynthesis of Tumor Necrosis Factor alpha (TNF-α) by UV Irradiation Human keratinocytes were cultured in a 12-well plate type incubator at a concentration of $10^4$. The plate was irradiated by UV-B at 30 mJ/cm². The media were exchanged with new medium containing 10 μM of each test substance (10 ppm of extract). After 6 to 24 hours of cultivation, the cells were harvested and subjected to ELISA (Pharmingen 555212) to determine the amount of produced tumor necrosis factor α (TNF-α). As the positive control, Wy-14,643 was used. The result is shown in Table 14 as comparative values, referred to 100 of UV control.

TABLE 14

| Test substances (10 μM) | TNF-α biosynthesis (%) |
|---|---|
| (−) EGCG | 35 |
| (−) GCG | 27 |
| (−) ECG | 32 |
| (−) CG | 37 |
| (+) C | 40 |
| Gallic acid | 36 |
| Caffeine | 39 |
| Quercetin | 27 |
| Kaempferol | 41 |
| Theobromine | 25 |
| Theophylline | 36 |
| Theanine | 30 |
| Quinic acid | 35 |
| Myricetin | 36 |
| Positive control | 30 |
| Green tea extract 1 | 25 |
| Green tea extract 2 | 30 |
| Catechin extract 1 | 15 |
| Catechin extract 2 | 12 |

From the result of Table 14, it was confirmed that the green tea extract, the catechin extract and each component of green tea reduced biosynthesis of tumor necrosis factor alpha by UV irradiation, thereby effectively preventing or improving dermal inflammation, reduction of dermal matrix material, deterioration of elasticity and wrinkle formation which may caused by UV irradiation.

[Experimental Example 11] Measurement of Inhibition Effect on Biosynthesis of Type I Collagenase (MMP-1) by UV Irradiation Human fibroblasts isolated from the skin of new born baby were cultured in a 48-well plate type incubator at a concentration of $10^4$. after 24 hours, the plate was irradiated by UV-A at 15 J/cm² and antibody against tumor necrosis factor alpha was added thereto in a concentration of 1 ug/ml. At the second day of cultivation, the supernatants were harvested and subjected to ELISA (AP biotech RPN2610) to determine the amount of produced type I collagenase. The result is shown in Table 15 as comparative values, referred to 100 of control which was not treated.

TABLE 15

| Treatment group | No-Antibody treated group | TNF-α treated group |
|---|---|---|
| UV-A irradiated group | 210 | 134 |
| TNF-α treated group | 250 | — |
| Control | 100 | 100 |

From the result of Table 15, it was confirmed that biosynthesis of type I collagenase was increased upon treatment of UV-A and the inflammatory mediator TNF-α and the increase of type I collagenase by UV irradiation was decreased upon treatment of antibody against TNF-α. Thus, it was confirmed when the inflammatory mediator TNF-α was increased by UV-A irradiation, type I collagenase was increased, while when the inflammatory mediator was blocked, the biosynthesis of type I collagenase was decreased.

When fibroblasts from a new born baby were treated with the following test substances, PPAR-α activators, the biosynthesis of type I collagenase was decreased, which was recovered upon treatment of the inflammatory mediator TNF-α.

To describe the experiment method in detail, human fibroblasts isolated from the skin of a new born baby were cultured in a 48-well plate type incubator at a concentration of $10^4$. After 24 hours, the plate was irradiated by UV-A at 15 J/cm². The media were exchanged with new medium containing 10 μM or 10 ppm of each test substance and TNF-α was added thereto in an amount of 10 ng/ml. At the second day of cultivation, the supernatants were harvested and subjected to ELISA (AP biotech RPN2610) to determine the amount of produced type I collagenase. As the positive control, Wy-14,643 and retinoic acid (RA) were used. The result is shown in Table 16 as comparative values, referred to 100 of negative control irradiated with UV.

TABLE 16

| Test substances | Type I collagenase biosynthesis (%) | |
| --- | --- | --- |
| (10 ppm) | UV-A irradiated group | UV-A + TNF-α treated group |
| (−) EGCG | 42 | 88 |
| (−) GCG | 43 | 86 |
| (−) ECG | 45 | 87 |
| (−) CG | 53 | 89 |
| (+) C | 45 | 86 |
| Gallic acid | 52 | 89 |
| Caffeine | 58 | 91 |
| Quercetin | 35 | 91 |
| Kaempferol | 48 | 94 |
| Theobromine | 32 | 90 |
| Theophylline | 40 | 92 |
| Theanine | 60 | 95 |
| Quinic acid | 75 | 98 |
| Myricetin | 52 | 97 |
| RA | 48 | 86 |
| Wy14643 | 60 | 92 |
| Green tea extract1 | 39 | 88 |
| Green tea extract2 | 44 | 89 |
| Catechin 1 | 38 | 87 |
| Catechin 2 | 40 | 89 |
| Negative control | 100 | 124 |

From the result of Table 16 and FIG. 1, it was confirmed that the green tea extract and each component of green tea reduced biosynthesis of type IV collagenase by UV irradiation, which was caused by decrease of biosynthesis of inflammatory mediators by activation of PPAR-α.

Now, concrete formulations of the anti-aging composition for external use on skin according to the present invention will be described. However, the composition for external use on skin according to the present invention is not limited thereto.

[Formulation 1] Skin Softener (Skin Lotion)

TABLE 17

| Ingredients | wt % |
| --- | --- |
| Purified water | Balance |
| Myricetin | 0.1 |
| Butylene glycol | 2.0 |
| Propylene glycol | 2.0 |
| Carboxyvinylpolymer | 0.1 |
| PEG-12 nonylphenyl ether | 0.2 |
| Polysorbate 80 | 0.4 |
| Ethanol | 10.0 |
| Triethanol amine | 0.1 |
| Preservative, pigment, flavor | Suitable amount |

[Formulation 2] Skin Lotion (Milk Lotion)

TABLE 18

| Ingredients | wt % |
| --- | --- |
| Purified water | Balance |
| Myricetin | 0.1 |
| Green tea extract | 0.1 |
| Beeswax | 4.0 |
| Polysorbate 60 | 1.5 |
| Sorbitan Sesquiolate | 1.5 |
| Liquid paraffin | 0.5 |
| Caprylic and capric triglyceride | 5.0 |
| Glycerine | 3.0 |
| Butylene glycol | 3.0 |
| Propylene glycol | 3.0 |
| Carboxyvinylpolymer | 0.1 |
| Triethanol amine | 0.2 |
| Preservative, pigment, flavor | Suitable amount |

[Formulation 3] Nourishing Cream

TABLE 19

| Ingredients | wt % |
| --- | --- |
| Purified water | Balance |
| Myricetin | 0.1 |
| Green tea catechin | 0.1 |
| Beeswax | 10.0 |
| Polysorbate 60 | 1.5 |
| PEG 60 hydrogenated castor oil | 2.0 |
| Sorbitan Sesquiolate | 0.5 |
| Liquid paraffin | 10.0 |
| Squalane | 5.0 |
| Caprylic and capric triglyceride | 5.0 |
| Glycerine | 5.0 |
| Putylene glycol | 3.0 |
| Propylene glycol | 3.0 |
| Triethanol amine | 0.2 |
| Preservative, pigment, flavor | Suitable amount |

[Formulation 4] Massage Cream

TABLE 20

| Ingredients | wt % |
| --- | --- |
| Purified water | Balance |
| Myricetin | 0.1 |
| epicatechin gallate (ECG) | 0.1 |
| Beeswax | 10.0 |
| Polysorbate 60 | 1.5 |
| PEG 60 hydrogenated castor oil | 2.0 |
| Sorbitan Sesquiolate | 0.8 |
| Liquid paraffin | 40.0 |
| Squalane | 5.0 |
| Caprylic and capric triglyceride | 4.0 |
| Glycerine | 5.0 |
| Butylene glycol | 3.0 |
| Propylene glycol | 3.0 |
| Triethanol amine | 0.2 |
| Preservative, pigment, flavor | Suitable amount |

[Formulation 5] Pack

TABLE 21

| Ingredients | wt % |
| --- | --- |
| Purified water | Balance |
| Myricetin | 0.1 |
| Catechin gallate (CG) | 0.1 |
| Polyvinyl alcohol | 13.0 |
| Sodium carboxymethyl cellulose | 0.2 |
| Glycerine | 5.0 |
| Allantoin | 0.1 |
| Ethanol | 6.0 |
| PEG-12 nonylphenyl ether | 0.3 |
| Polysorbate 60 | 0.3 |
| Preservative, pigment, flavor | Suitable amount |

[Formulation 6] Skin Softener (Skin Lotion)

TABLE 22

| Ingredients | Content (wt %) |
| --- | --- |
| Purified water | To 100 |
| Green tea catechin | 0.0025 |
| Theanine | 1 |
| Butylene glycol | 2.0 |
| Propylene glycol | 2.0 |
| Carboxyvinylpolymer | 0.1 |
| PEG-12 nonylphenyl ether | 0.2 |
| Polysorbate 80 | 0.4 |
| Ethanol | 10.0 |

TABLE 22-continued

| Ingredients | Content (wt %) |
| --- | --- |
| Triethanol amine | 0.1 |
| Preservative, pigment, flavor | Suitable amount |

[Formulation 7] Skin Lotion (Milk Lotion)

TABLE 23

| Ingredients | Content (wt %) |
| --- | --- |
| Purified water | To 100 |
| Green teacatechin | 0.0025 |
| Theanine | 1 |
| Beeswax | 4.0 |
| Polysorbate 60 | 1.5 |
| Sorbitan Sesquiolate | 1.5 |
| Liquid paraffin | 0.5 |
| Caprylic and capric triglyceride | 5.0 |
| Glycerine | 3.0 |
| Butylene glycol | 3.0 |
| Propylene glycol | 3.0 |
| Carboxyvinylpolymer | 0.1 |
| Triethanol amine | 0.2 |
| Preservative, pigment, flavor | Suitable amount |

[Formulation 8] Nourishing Cream

TABLE 24

| Ingredients | Content (wt %) |
| --- | --- |
| Purified water | To 100 |
| Green tea catechin | 0.0025 |
| Theanine | 1 |
| Beeswax | 10.0 |
| Polysorbate 60 | 1.5 |
| PEG 60 hydrogenated castor oil | 2.0 |
| Sorbitan Sesquiolate | 0.5 |
| Liquid paraffin | 10.0 |
| Squalane | 5.0 |
| Caprylic and capric triglyceride | 5.0 |
| Glycerine | 5.0 |
| Butylene glycol | 3.0 |
| Propylene glycol | 3.0 |
| Triethanol amine | 0.2 |
| Preservative, pigment, flavor | Suitable amount |

[Formulation 9] Massage Cream

TABLE 25

| Ingredients | Content (wt %) |
| --- | --- |
| Purified water | To 100 |
| Green tea catechin | 0.0025 |
| Theanine | 1 |
| Beeswax | 10.0 |
| Polysorbate 60 | 1.5 |
| PEG 60 hydrogenated castor oil | 2.0 |
| Sorbitan Sesquiolate | 0.8 |
| Liquid paraffin | 40.0 |
| Squalane | 5.0 |
| Caprylic and capric triglyceride | 4.0 |
| Glycerine | 5.0 |
| Butylene glycol | 3.0 |
| Propylene glycol | 3.0 |
| Triethanol amine | 0.2 |
| Preservative, pigment, flavor | Suitable amount |

[Formulation 10] Pack

TABLE 26

| Ingredients | Content (wt %) |
| --- | --- |
| Purified water | To 100 |
| Green tea catechin | 0.0025 |
| Theanine | 1 |
| Polyvinyl alcohol | 13.0 |
| Sodium carboxymethyl cellulose | 0.2 |
| Glycerine | 5.0 |
| Allantoin | 0.1 |
| Ethanol | 6.0 |
| PEG-12 nonylphenyl ether | 0.3 |
| Polysorbate 60 | 0.3 |
| Preservative, pigment, flavor | Suitable amount |

[Formulation 11] Skin Softener (Skin Lotion)

TABLE 27

| Ingredients | wt % |
| --- | --- |
| Purified water | Balance |
| Epigallocatechin (EGCG) | 0.1 |
| Butylene glycol | 2.0 |
| Propylene glycol | 2.0 |
| Carboxyvinylpolymer | 0.1 |
| PEG-12 nonylphenyl ether | 0.2 |
| Polysorbate 80 | 0.4 |
| Ethanol | 10.0 |
| Triethanol amine | 0.1 |
| Preservative, pigment, flavor | Suitable amount |

[Formulation 12] Skin Lotion (Milk Lotion)

TABLE 28

| Ingredients | wt % |
| --- | --- |
| Purified water | Balance |
| Green tea extract | 0.1 |
| Beeswax | 4.0 |
| Polysorbate 60 | 1.5 |
| Sorbitan Sesquiolate | 1.5 |
| Liquid paraffin | 0.5 |
| Caprylic and capric triglyceride | Suitable amount |

[Formulation 13] Nourishing Cream

TABLE 29

| Ingredients | wt % |
| --- | --- |
| Purified water | Balance |
| Kaempferol | 0.1 |
| Beeswax | 10.0 |
| Polysorbate 60 | 1.5 |
| PEG 60 hydrogenated castor oil | 2.0 |
| Sorbitan Sesquiolate | 0.5 |
| Liquid paraffin | 10.0 |
| Squalane | 5.0 |
| Caprylic and capric triglyceride | 5.0 |
| Glycerine | 5.0 |
| Putylene glycol | 3.0 |
| Propylene glycol | 3.0 |
| Triethanol amine | 0.2 |
| Preservative, pigment, flavor | Suitable amount |

INDUSTRIAL APPLICABILITY

The composition for external use on skin according to the present invention comprises at least one of catechins and flavonols which are components of green tea as an active ingredient to reduce biosynthesis of gelatinase (MMP-2, MMP-9) and increase biosynthesis of type IV collagen, type VII collagen and laminin 10/11, thereby inhibiting decomposition and promoting generation of the dermis-epidermis junction and protecting the dermis-epidermis junction.

The invention claimed is:

1. A method of promoting biosynthesis of collagen and improving at least one of skin wrinkle and elasticity comprising externally applying on the skin of a subject in need thereof a composition comprising a mixture of a catechin and theanine as active ingredients,
   wherein the content of the catechin in the composition is 0.0004 wt % to 0.025 wt % with regard to the total weight of the composition,
   wherein the content of the theanine in the composition is 0.01 wt % to 2.5 wt % with regard to the total weight of the composition,
   wherein a mixed weight ratio of the catechin to the theanine is 1:25~1:100, and wherein the catechin is at least one selected from the group consisting of (−)GCG (gallocatechin gallate), (−)ECG (epicatechin gallate), and (−)CG (catechin gallate).

2. The method of claim 1, wherein the composition is a cosmetic composition.

3. The method of claim 2, wherein the cosmetic composition contains a cosmetically acceptable additive.

4. The method of claim 1, wherein the catechin is at least one selected from the group consisting of (−)ECG (epicatechin gallate) and (−)CG (catechin gallate).

5. A method of promoting biosynthesis of collagen and improving at least one of skin wrinkle and elasticity comprising externally applying on the skin of a subject in need thereof a composition comprising active ingredients consisting of a catechin and theanine,
   wherein the content of the catechin in the composition is 0.0004 wt % to 0.025 wt % with regard to the total weight of the composition,
   wherein the content of the theanine in the composition is 0.01 wt % to 2.5 wt % with regard to the total weight of the composition,
   wherein a mixed weight ratio of the catechin to the theanine is 1:25~1:100, and
   wherein the catechin is at least one selected from the group consisting of (−)GCG (gallocatechin gallate), (−)ECG (epicatechin gallate), and (−)CG (catechin gallate).

* * * * *